(12) United States Patent
Gregg et al.

(10) Patent No.: US 8,688,206 B2
(45) Date of Patent: Apr. 1, 2014

(54) VISUALIZATION OF MYOCARDIAL INFARCT SIZE IN DIAGNOSTIC ECG

(75) Inventors: Richard E. Gregg, Westford, MA (US); Sophia Huai Zhou, Briarcliff Manor, NY (US)

(73) Assignee: Koninklijke Philips N.V., Eindhoven (NL)

(*) Notice: Subject to any disclaimer, the term of this patent is extended or adjusted under 35 U.S.C. 154(b) by 0 days.

(21) Appl. No.: 13/643,114

(22) PCT Filed: Apr. 25, 2011

(86) PCT No.: PCT/IB2011/051781
§ 371 (c)(1),
(2), (4) Date: Oct. 24, 2012

(87) PCT Pub. No.: WO2011/135507
PCT Pub. Date: Nov. 3, 2011

(65) Prior Publication Data
US 2013/0060156 A1 Mar. 7, 2013

Related U.S. Application Data

(60) Provisional application No. 61/328,671, filed on Apr. 28, 2010.

(51) Int. Cl.
*A61B 5/04* (2006.01)
(52) U.S. Cl.
USPC .......................................................... 600/523
(58) Field of Classification Search
USPC .................................. 600/523, 509; 382/128
See application file for complete search history.

(56) References Cited

U.S. PATENT DOCUMENTS

| 6,389,310 | B1 | 5/2002 | Demonceau et al. | |
|---|---|---|---|---|
| 2002/0016551 | A1* | 2/2002 | Selvester et al. | 600/523 |
| 2005/0020903 | A1 | 1/2005 | Krishnan et al. | |
| 2006/0100518 | A1 | 5/2006 | Krishnan | |
| 2006/0253162 | A1 | 11/2006 | Zhang et al. | |
| 2006/0264770 | A1* | 11/2006 | Wellens et al. | 600/509 |
| 2012/0027276 | A1* | 2/2012 | Chono | 382/128 |

FOREIGN PATENT DOCUMENTS

| WO | 2010099386 A1 | 9/2010 |
|---|---|---|
| WO | 2011089488 A1 | 7/2011 |

OTHER PUBLICATIONS

D.G. Strauss et al.; "The QRS Complex—A Biomarker that "Images" the Heart" QRS Score to Quantify Myocardial Scar in the Presence of Normal and Abnormal Ventricular Condution; Journal of Electrocardiology 42 (2009) pp. 85-96.
B. Milan Horacek et al.; "Development of an Automated Selvester Scoring System for Estimating the Size of Myocardial Infarction from the Electrocardiogram"; Journal of Electrocardiology 39 (2006) pp. 162-168.
D.G. Strauss et al; "Imaging Myocardial Scar and Arrhythmic Risk Prediction—A Role for the Electorcardiogram"; Journal of Electrocardiology 42 (2009) pp. 138.e1-138.e8.

* cited by examiner

*Primary Examiner* — Niketa Patel
*Assistant Examiner* — Robert N Wieland

(57) ABSTRACT

The segments of an anatomically corresponding bull's eye graph familiar to echocardiologists is annotated by coloring those segments for which ECG data indicates the presence of myocardial infarction injury. In an illustrated example, segments are colored with a second color when the ECG data corresponding to those segments are indicated as being the site of a coronary occlusion. The segments of the bull's eye graph may be colored in a third color with the results of a diagnostic imaging exam, such as by coloring segments exhibiting wall motion abnormalities with a third color.

14 Claims, 11 Drawing Sheets

| Field | I | II | III | aVR | aVL | aVF | V1 | V2 | V3 | V4 | V5 | V6 |
|---|---|---|---|---|---|---|---|---|---|---|---|---|
| P AMP | 140 | 130 | 50 | -140 | 90 | 70 | 60 | 80 | 80 | 80 | 100 | 100 |
| P DUR | 88 | 132 | 64 | 128 | 92 | 120 | 44 | 96 | 124 | 116 | 116 | 160 |
| P AREA | 21 | 23 | 3 | -23 | 12 | 11 | 5 | 8 | 12 | 14 | 16 | 16 |
| P NOTCH | | | | | | | | | | | | |
| P' AMP | | | -50 | | | | -60 | | | | | |
| P' DUR | | | 64 | | | | 80 | | | | | |
| P' AREA | | | -3 | | | | -6 | | | | | |
| Q AMP | -140 | | | -520 | -350 | | -1360 | -2910 | | -30 | | |
| Q DUR | 36 | | | 84 | 52 | | 84 | 100 | | 16 | | |
| R AMP | 660 | 830 | 690 | | 850 | 760 | | | 20 | 600 | 780 | 800 |
| R DUR | 56 | 56 | 56 | | 40 | 56 | | | 12 | 28 | 56 | 76 |
| S AMP | | -450 | -1070 | | | -760 | | | -280 | -1130 | -240 | |
| S DUR | | 36 | 48 | | | 40 | | | 28 | 60 | 32 | |
| R' AMP | | | | | | | | | 30 | | | |
| R' DUR | | | | | | | | | 8 | | | |
| S' AMP | | | | | | | | | -2440 | | | |
| S' DUR | | | | | | | | | 64 | | | |
| V.A.T. | 76 | 44 | 44 | | 72 | 40 | | | 44 | 32 | 36 | 40 |
| QRS PPK | 800 | 1280 | 1760 | 520 | 1200 | 1520 | 1360 | 2910 | 2470 | 1730 | 1020 | 800 |
| QRS DUR | 92 | 92 | 104 | 84 | 92 | 96 | 84 | 100 | 112 | 104 | 88 | 76 |
| QRS AREA | 41 | 32 | -10 | -37 | 26 | 10 | -115 | -239 | -196 | -64 | 34 | 55 |
| QRS NOT... | | | | | | | | | | | | |
| DELTA | | | | | | | | | | | | |
| ST ON | -60 | -50 | | 60 | -30 | -30 | 120 | 150 | 120 | | -60 | -60 |
| ST MID | -50 | -50 | | 40 | -20 | -20 | 180 | 250 | 170 | 10 | -50 | -50 |
| ST 80ms | -50 | -50 | -10 | 50 | -20 | -30 | 180 | 280 | 210 | 20 | -50 | -50 |
| ST END | -50 | -50 | 10 | 10 | -20 | -10 | 250 | 350 | 200 | 20 | -60 | -30 |
| ST DUR | 112 | 72 | 120 | 176 | 112 | 136 | 124 | 104 | 80 | 104 | 96 | 176 |
| ST SLOPE | 3 | 1 | | -5 | 2 | 3 | 21 | 37 | 26 | 6 | | 2 |
| ST SHAPE | STR | STR | STR | STR | STR | STR | STR | STR | STR | STR | STR | STR |
| T AMP | -50 | -60 | 200 | -100 | -120 | 180 | 350 | 620 | 460 | 90 | -70 | 110 |
| T DUR | 144 | 92 | 200 | 152 | 200 | 196 | 216 | 232 | 200 | 172 | 112 | 196 |
| T NOTCH | | | | | | | | | | | | |
| T' AMP | | 190 | | | | | | | | | 110 | |
| T' DUR | | 176 | | | | | | | | | 188 | |
| T' AREA | | 37 | | | | | | | | | 23 | |
| PR INT | 148 | 148 | 128 | 156 | 112 | 152 | 156 | 148 | 136 | 148 | 152 | 156 |
| PR SEG | 12 | 16 | 16 | 20 | 12 | 16 | 24 | 76 | 20 | 16 | 20 | 20 |
| QT INT | 372 | 436 | 448 | 436 | 424 | 452 | 396 | 408 | 416 | 404 | 476 | 472 |
| GROUP | 1 | 1 | 1 | 1 | 1 | 1 | 1 | 1 | 1 | 1 | 1 | 1 |
| QUALITY | MA... | MA... | NL | MA... | NL | MA... | NL | NL | NL | NL | MA... | NL |
| NOISE | T | T | | T | | T | | | | | T | |

VISUALIZATION OF MYOCARDIAL INFARCT SIZE IN DIAGNOSTIC ECG

This invention relates to diagnostic electrocardiographic (ECG) systems and, in particular, to diagnostic ECG systems which present a visualization of the size of a myocardial infarct in a way that is familiar to those specializing in medical diagnostic imaging such as MRI, CT, ultrasound, and nuclear medicine.

Diagnostic ECG records and analyzes the ECG signals received simultaneously on multiple leads. The lead number is generally twelve to eighteen, and the lead signals are produced from the body's electrical signals received by ten to sixteen electrodes. Myocardial infarct (MI) size can be estimated by ECG characteristics such as a deepened Q wave, reduced R-wave amplitude, elevated ST segments and inverted T wave on various leads. The greater the infarct size, the greater the number of leads that display such abnormal characteristics.

A numeric MI score can be generated from these results as a reference for cardiologists or emergency physicians in triage or treatment decision support. Several ECG algorithms exist to estimate the size of an acute myocardial infarction (AMI) or an evolving myocardial infarction. The algorithms estimate the size of the MI in terms of percent of left ventricular (LV) mass affected. For example, the ST segment deviation score (the sum of ST segment deviation in all 12 leads) can be used as an estimate of the ischemic LV mass at risk of infarct. More than 1.5 mV of elevation indicates a large area at risk. Furthermore, ECG algorithms have been developed which are able to identify the location of a lesion within the coronary artery tree. In that case, the ischemic area at risk of infarction is the area covered by the coronary artery in question. A. Bayes de Luna, Anton Gorgels and others have shown how the culprit artery can be determined with these algorithms. ECG algorithms are accurate enough to predict not only the identity of the culprit coronary artery, but the proximal or distal location of the infarct within the coronary artery tree. In addition, an ECG algorithm can indicate where a coronary artery is occluded if the ECG in question is an acute case (and not a chronic or old infarction). The Selvester MI scoring system is a well established and well validated technique for assessing chronic and evolving MI (days or months old). The approach of A. Bayes de Luna and others for estimating acute MI size by the magnitude and distribution of ST elevation and depression on the 12-lead ECG would be used in the acute MI case. For MI cases of an in-between age, usually called recent (not quite acute, not quite chronic), both the acute MI and the chronic MI size algorithms apply.

Echocardiography is used to detect acute infarct/ischemia by detecting regional wall motion abnormalities (WMA) in the left ventricle. Regional WMA show ischemic or infarcted non-functional ventricular tissue that is not actively contracting but being dragged along by surrounding healthy myocardial tissue. An established diagnostic imaging exam of cardiac performance is the stress echocardiogram study, in which the heart is imaged ultrasonically. In a stress echo exam, ultrasound images of the heart are acquired at the outset when the patient is resting. These images are standard cross-sectional images of long axis and short axis views of the heart during the rest stage. The patient then exercises to raise the heart rate above a given level. This may be done by having the patient run on a treadmill, and it may also be done by injection of a pharmacological agent. The same standard images are acquired during the exercise stage when the heart is beating at a high rate. The pre- and post-exercise images are then compared, generally by first synchronizing the different heartbeats of the image loops so that they move together. Characteristics which are assessed include wall motion abnormalities and systolic thickening (tissue deformation) of the myocardium. Qualitative and quantitative analysis is performed on the images using tissue Doppler, speckle image analysis, i.e., strain quantification analysis, or any other ultrasonic detection of myocardial deformation. Left ventricular filling, ejection fraction, and ejection velocities may also be assessed. The results of the diagnostic imaging study are frequently illustrated on a 17 segment bull's eye graph. The bull's eye graph has been standardized in cardiac imaging diagnostics and is well recognized for its ease and convenience in MI description in relation to human anatomy.

A problem addressed by the present invention is the simplification of the link between 12-lead ECG reporting and cardiac imaging. Usually cardiologists familiar with cardiac imaging are less familiar with the precise ECG algorithms for determining a culprit coronary artery in the evolution of infarction. Imagining the way the ECG vector is generated in three dimensions is intuitive to ECG experts, but very difficult for the non-expert. Accordingly it is an objective of the present invention to present a visualization of diagnostic ECG data and in particular myocardial infarct size in a format that is easily understandable to experts in medical diagnostic imaging.

In accordance with the principles of the present invention, diagnostic ECG results which indicate the size of a myocardial infarct are presented in a format which is familiar in cardiac imaging. An apparatus and preferred method are described which use a diagnostic ECG system to acquire ECG lead signals and calculate ECG parameters of interest in sizing a myocardial infarct. The ECG parameters are used to calculate the MI size and location, preferably using the Selvester scoring system. The Selvester score identifies the segments in an Ideker ECG 12-segment LV model which are infarcted. The identified segments are mapped to a diagnostic imaging 17-segment bull's eye graph. Segments which are indicated as infarcted are colored with a first color or shading. In an extension of the present invention, the ECG criteria of A. Bayes de Luna or Wellens are used to determine the probable location of an occlusion in the coronary artery tree if the ECG is characterized by ST elevation from myocardial infarction. The coronary artery occlusion site is mapped to ischemic segments of the bull's eye graph and colored with a second color or shading. Segments of the bull's eye graph may, if desired, be further annotated with one or more colors denoting ultrasonically derived results such as wall motion abnormalities. Coloring the bull's eye graph, familiar in imaging for wall motion abnormality indication, links the ECG results to imaging results in a format familiar to imaging experts.

In the drawings:

FIG. 6 illustrates parameters typically calculated by a diagnostic ECG analysis module.

Figure 1:
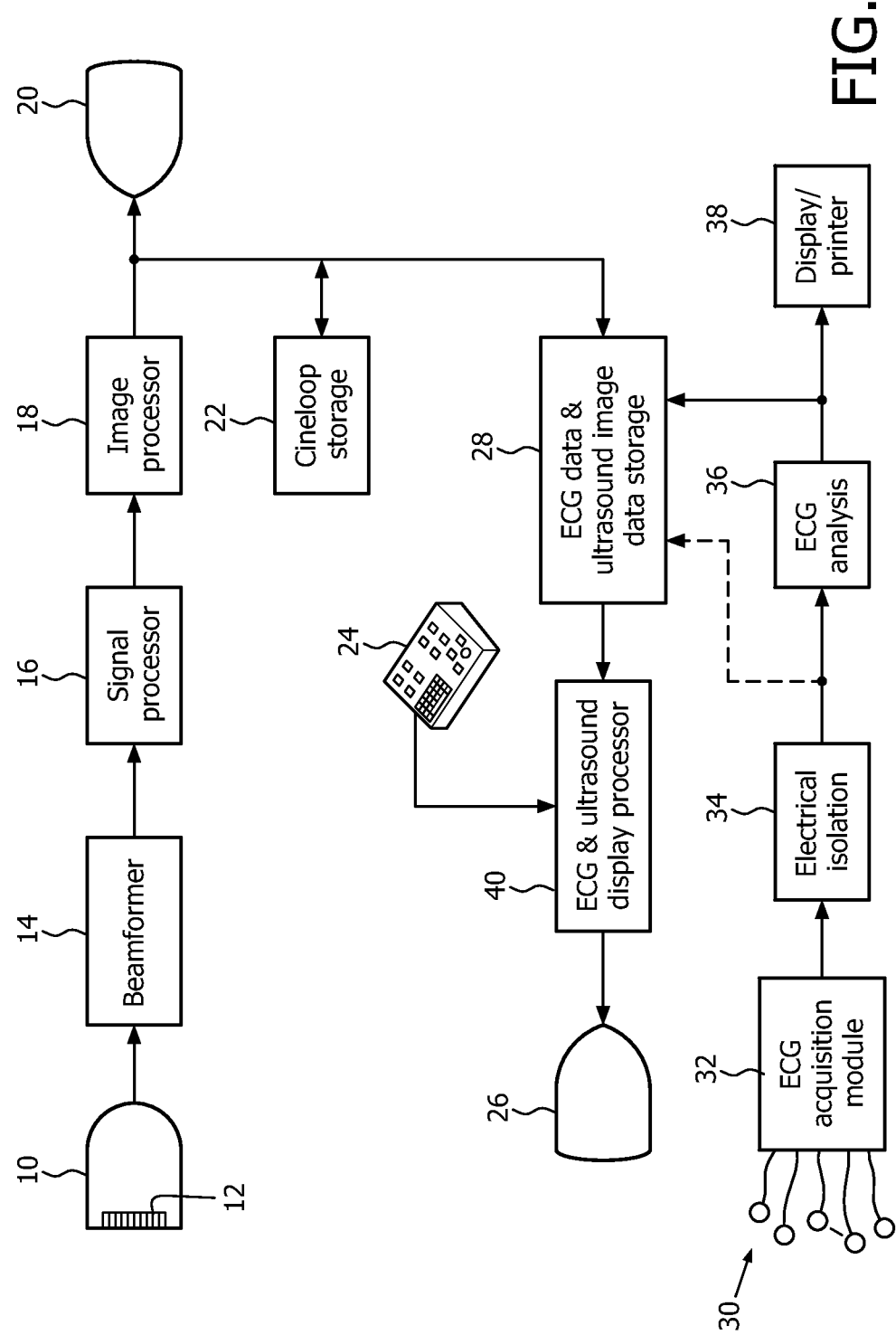
FIG. 1 illustrates in block diagram form an ultrasound and ECG diagnostic system constructed in accordance with the principles of the present invention.

Referring first to FIG. 1, a display system for ultrasound images and ECG lead traces is shown in block diagram form. The major subsystems of an ultrasound system are shown at the top of the drawing. An ultrasound probe 10 with an array transducer 12 transmits ultrasound waves to the heart of a patient and receives echoes in response. The echo signals received by the individual transducer elements of the array are processed by a beamformer 14 to form coherent echo signals relating to specific points in the body. The echo signals are processed by a signal processor 16. Signal processing may include separation of harmonic echo signal components for harmonic imaging and clutter removal, for example. The processed signals are arranged into images of a desired format by an image processor 18. The images are displayed on an ultrasound system display 20. Live image loops are stored in Cineloop® storage 22 for later recall an analysis.

The ultrasound images used in stress echo are real time (live) images of the heart as it is beating. A nominal display rate for live ultrasound images is 30 frames per second. The images may be either two-dimensional or three-dimensional images of the heart. In the examples shown below, two-dimensional images are shown. The standard views for stress echo studies are parasternal long axis views such as the parasternal 3-chamber view, and parasternal short axis views at the base, mid-cavity, and apical levels of the heart. Parasternal images are acquired by transmitting and receiving ultrasound signals through the intercostal regions between the ribs. Other standard views in stress echo exams include apical 4-chamber, 2-chamber and long axis views. Apical views are acquired by placing the probe below the rib cage and transmitting and receiving ultrasound while the probe is viewing the heart from below, from the apex. The outflow tract of the heart is visible in the 3-chamber view, whereas the outflow tract cannot be seen in a 4-chamber view. A 2-chamber view shows only the left ventricle and the left atrium. The most common short axis view used is the mid-view, which captures the papillary muscle as an anatomical reference in the image.

The major subsystems of a diagnostic ECG system are shown at the bottom of the drawing. Electrodes 30 are attached to the skin of the patient at specific locations on the body to acquire ECG signals. Usually the electrodes are disposable conductors with a conductive adhesive gel surface that sticks to the skin. Each conductor has a snap or clip that snaps or clips onto an electrode wire of the ECG system. A typical ECG system will have twelve leads (ten electrodes), which may be expanded with additional leads on the back of the patient for up to sixteen leads. Extended lead sets with up to eighteen leads may be used. In addition, fewer leads such as 3-lead (EASI and other), 5-, and 8-lead sets can also be used to derive 12 leads, but with reduced accuracy. The acquired ECG signals, which are on the order of millivolts, are preconditioned by an ECG acquisition module 32 which performs processing such as amplification, filtering and digitizing of the ECG signals. The electrode signals are coupled to an ECG analysis module 36, generally by means of an electrical isolation arrangement 34 that protects the patient from shock hazards and also protects the ECG system when the patient is undergoing defibrillation, for instance. Optical isolators are generally used for electrical isolation. The ECG analysis module 36 combines the signals from the electrodes in various ways to form the desired lead signals, and performs other functions such as signal averaging, heart rate identification, and identifies signal characteristics such as the QRS complex, the P-wave, T-wave, and other characteristics such as elevation seen in the S-T interval. The processed ECG information is then displayed on an image display or printed in an ECG report by an output device 38.

In accordance with the principles of the present invention, the ultrasound images and the ECG lead data are coupled to a combined ultrasound image and ECG display system. In FIG. 1 the ultrasound and ECG information is coupled to an ECG data and ultrasound image data storage device 28. In a typical arrangement the ultrasound system is a stand-alone ultrasound system and the ECG system is a stand-alone cardiograph. Data from the two systems may be directly coupled to the ECG data and ultrasound image data storage device 28, or it may be coupled to the device 28 over a network, or may be ported into the device 28 on one or a plurality of storage media devices. The ECG data and ultrasound image data is then processed for common display by an ECG and ultrasound display processor 40. The merged data is then displayed on an image display 26. A control panel 24 is operated by a user to control the processing and display of the merged data. In a typical implementation, the storage device 28, the processor 40, the control panel 44 and the display 26 are a workstation or a separate computer system.

Figure 2:
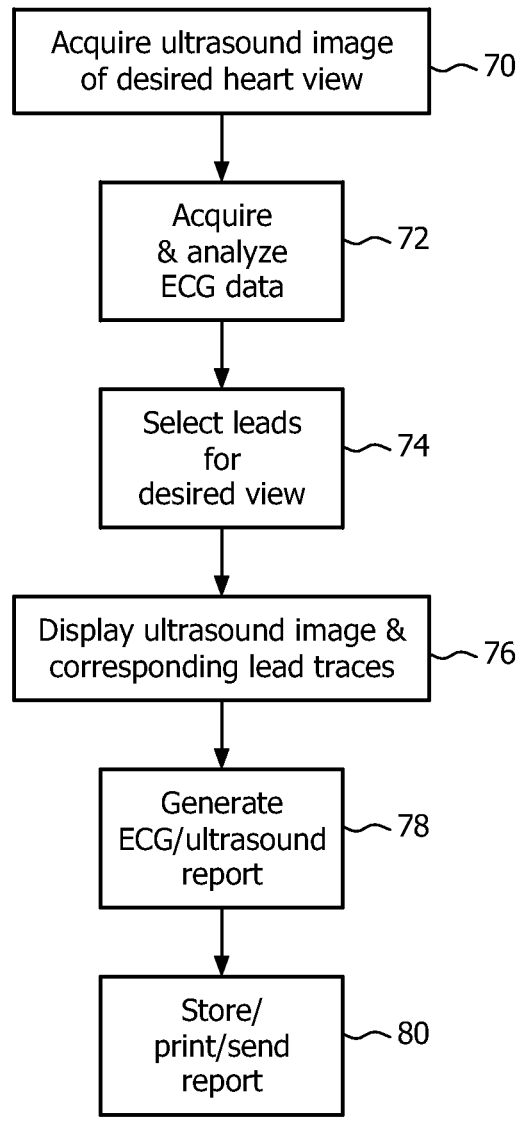
FIG. 2 illustrates a flowchart for acquiring and displaying selected ultrasound images and ECG lead traces in accordance with the present invention.
Figure 3:
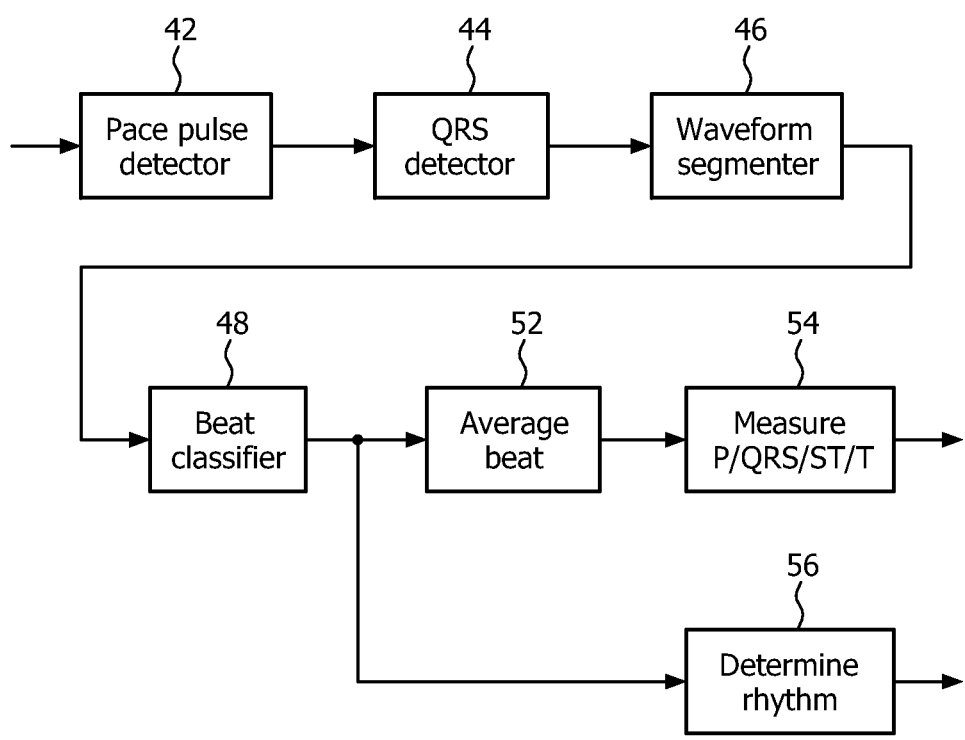
FIG. 3 is a block diagram of the analysis module of a typical diagnostic ECG system.

FIG. 2 illustrates a sequence of operations for acquiring and displaying ultrasound images and ECG lead data in a common display. In step 70 the ultrasound and ECG display system acquires one or more ultrasound images of a desired heart view. The desired view of the heart can be a long or short axis view, a parasternal or apical view, and can be a two- three- or four-chamber view, for example. Next, or concurrently, the ultrasound and ECG display system acquires an ECG lead dataset at step 72. The display system may display all of the twelve ECG lead signals with the ultrasound images, but preferably the display system displays ECG lead signals with ultrasound images that correspond to the view of those ultrasound images. The system may be pre-programmed with certain ECG leads that correspond with specific ultrasound image views, and such programming may be factory-installed and fixed. Preferably, the ECG leads selected for the different ultrasound views are not fixed, but can be varied by the user. In that case, and if the user has a specific set of lead signals to be displayed with a given ultrasound view, the user will select the ECG leads to display with a specific desired view in step 74. At step 76 the display system displays an ultrasound image or loop and its corresponding ECG lead traces on the display 26. The system may also generate an ECG/ultrasound report in step 78 and store or print or transmit the report to another user such as a referring physician in step 80.

Figure 4:
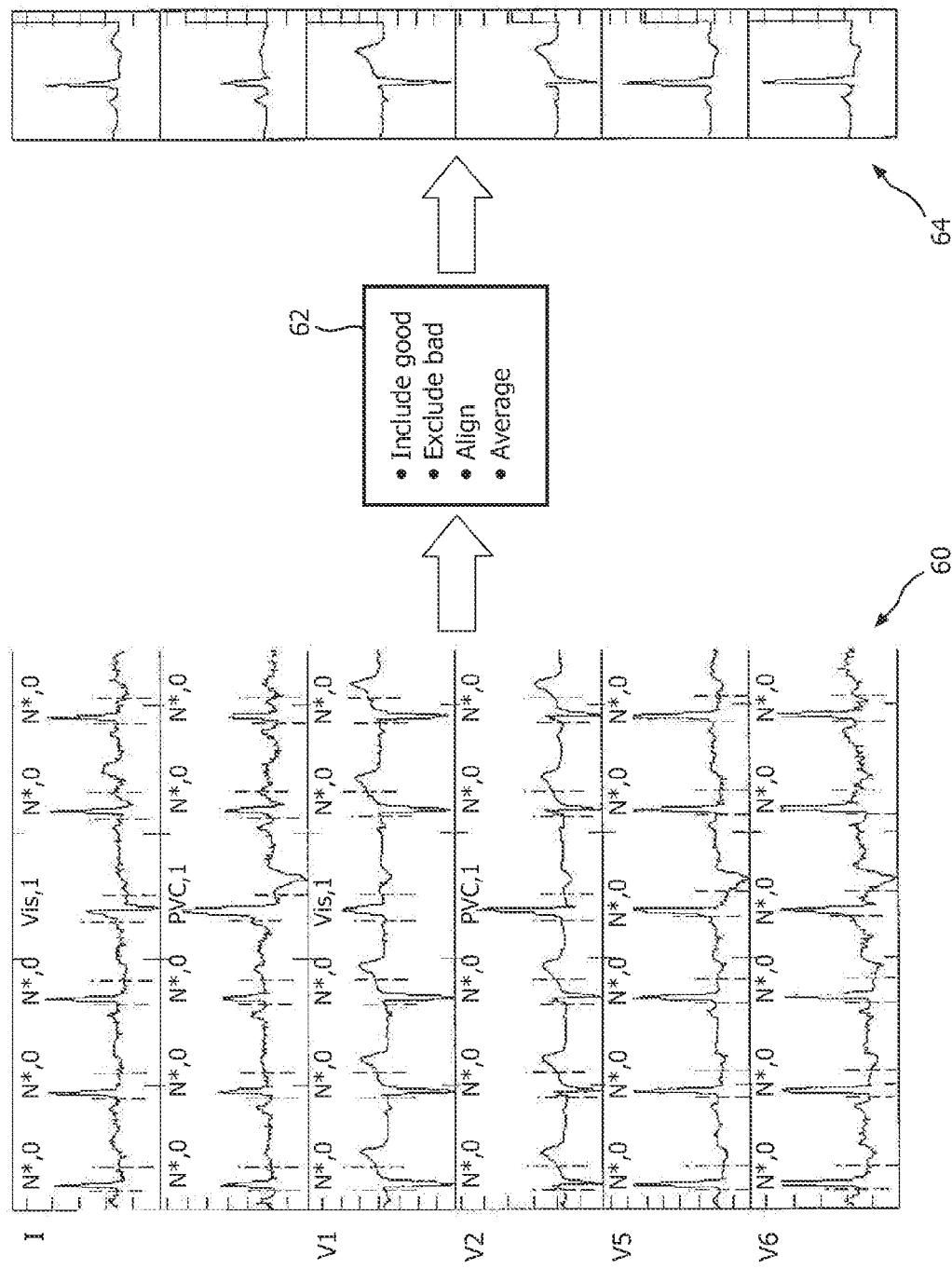
FIG. 4 illustrates the processing of ECG trace data to provide information about the heartbeat and its rhythm.
Figure 5:
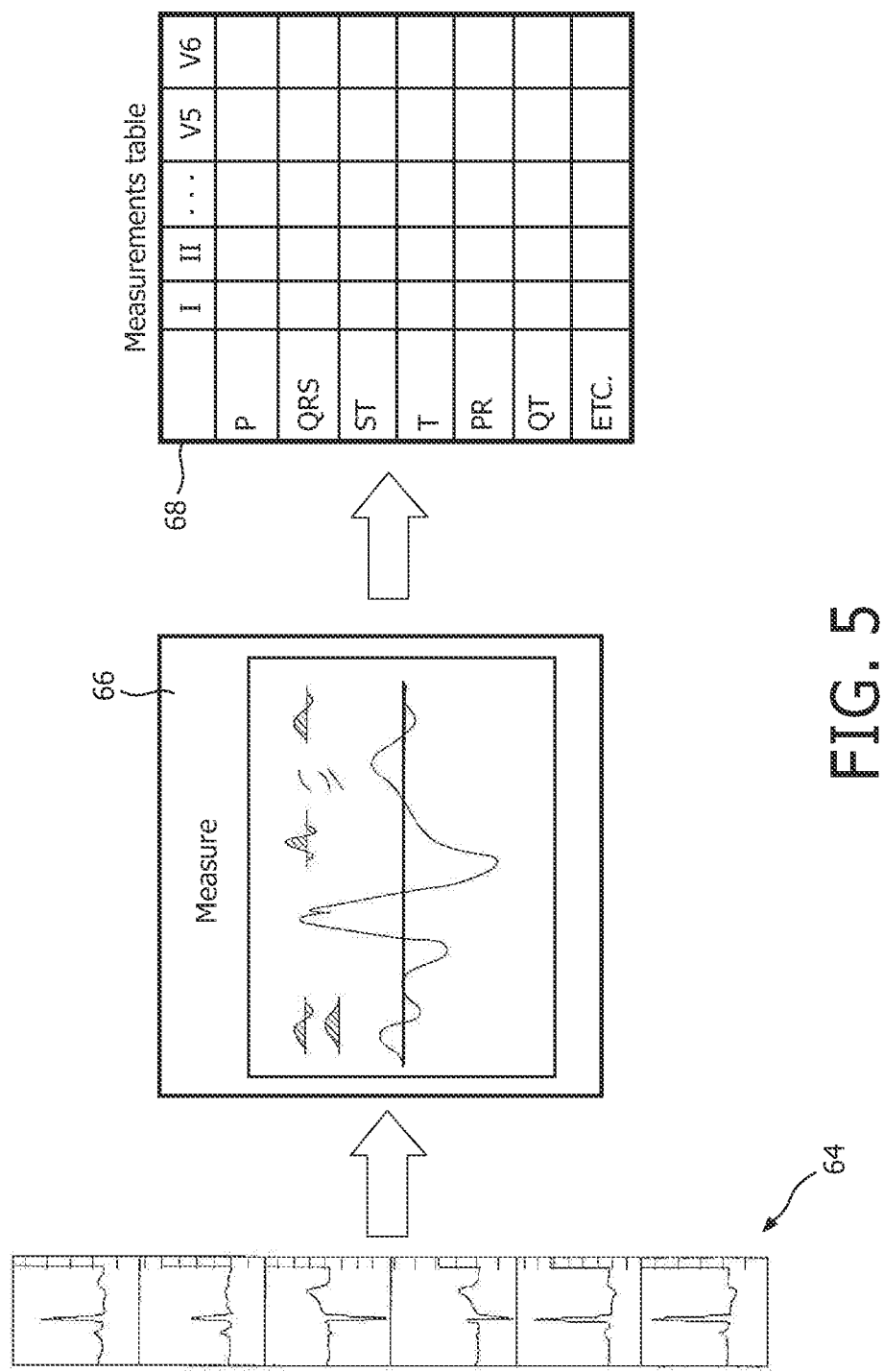
FIG. 5 illustrates the measurement of different parameters of an ECG trace.
Figure 7:
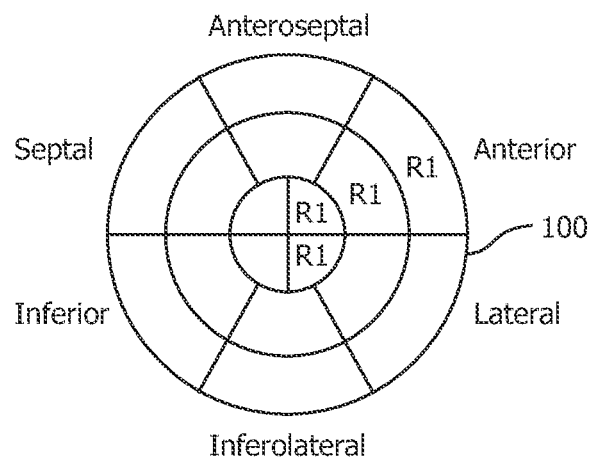
FIG. 7 illustrates a bullet scorecard which is visually marked to indicate suspect regions of a heart.

FIG. 7 is a block diagram of the ECG analysis module of the diagnostic ECG system of FIG. 1. A pace pulse detector 42 identifies and sets aside electrical spikes and other electrical abnormalities produced by a pacemaker for patients who are wearing one. A QRS detector 44 detects the dominant pulse of the electrical traces. Delineation of the QRS complex forms the basis for detecting the lesser perturbations of the trace, which is performed by the waveform segmenter 46. The waveform segmenter delineates the full sequence of trace segments including the P wave and the Q to U segments of the ECG trace. With each waveform now fully delineated, a beat classifier 48 compares each new beat with previous beats and classifies beats as normal (regular) for the individual or abnormal (irregular). The classification of the beats enables an average beat analyzer 52 to define the characteristics of a normal heartbeat and the amplitudes and segment durations of an ECG waveform are measured at 54. The beat classifications are used to determine the heart rhythm at 56. FIGS. 4, 5 and 6 are functional illustrations of this ECG trace processing. At the left side of FIG. 4 is a series 60 of ECG traces from leads I, II, V1, V2, V5 and V6. The beat classifier 48 compares the various beat characteristics and has classified some of the beats as normal (N*, 0). For example, all of the beats from leads V5 and V6 have been classified as normal in this example. The other four leads contain a beat exhibiting the characteristics of premature ventricular contraction (PVC, 1). At 62 the ECG system aggregates the characteristics of the normal beats, excludes characteristics of the abnormal beats, aligns the beats in time and averages them to produce an average beat. The traces at 64 illustrate the traces of an average beat for the six leads shown in this example. In FIG. 5 the average beat traces 64 of the six leads are measured for various characteristics shown at 66, such as the amplitudes and durations of the Q wave, the R wave, and the T wave and inter-wave intervals such as QRS, ST and QT. The measurements are illustrated as recorded in a measurement table 68 for the six leads of this example. An example of a complete measurement table for a 12-lead system is shown in FIG. 6.

A bullet scorecard is commonly used in ultrasound to record measurements taken at specific segments of the myocardium which correspond to specific segments of the scorecard. In general, a bullet scorecard is an LV segmental display. Ultrasound measurements which are recorded on a bullet scorecard include wall motion values, strain rate values, and perfusion values. The values may be shown quantitatively, but a qualitative bullet scorecard is often used to quickly draw the attention of the clinician to a specific heart region. For example, the bullet scorecard 100 in FIG. 7 has been filled in with a green color where wall motion or myocardial perfusion is normal, and has been filled in with red (the darker shade) where abnormal wall motion or myocardial perfusion has been detected. In this example, the attention of the clinician is immediately drawn to the anterior side of the heart anatomy where the abnormality is indicated.

Figure 8A:
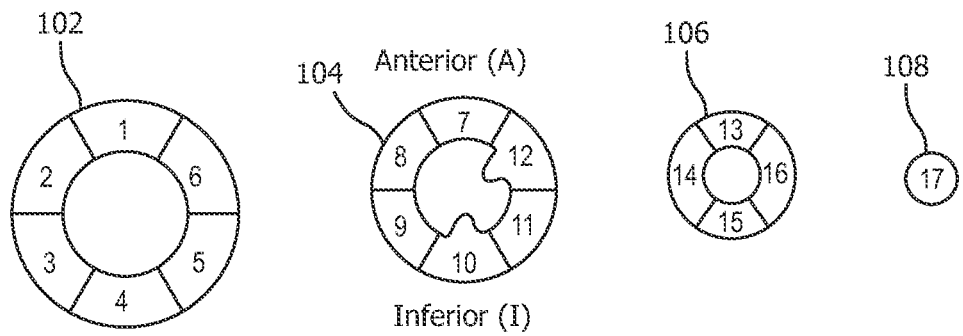
FIGS. 8a and 8b illustrate the layout of an ECG bull's eye graph of the present invention.
Figure 8B:
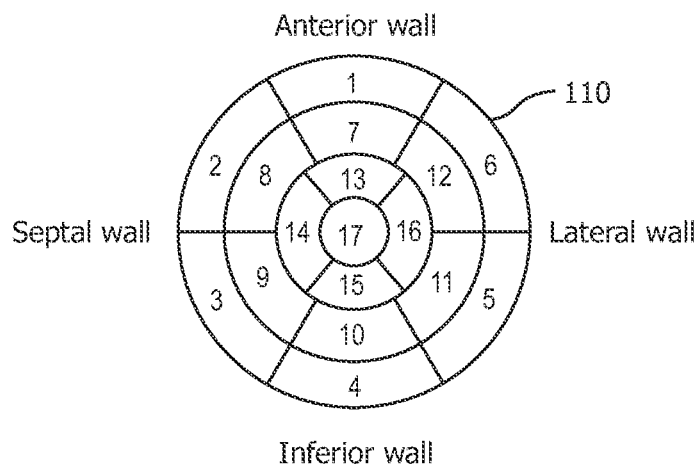

In accordance with the principles of the present invention, a bull's eye graph has segments filled in with ECG data corresponding to the anatomical regions of the segments of the graph. The segments of a bull's eye graph have been numbered in correspondence with the anatomy of the heart in a standardized pattern as shown in FIG. 8a. Myocardial segments of a basal short axis ultrasound view 102, near the mitral valve plane, are numbered 1 through 6 as shown at the left side of FIG. 8a. The smaller circle 104 represents the segments of a mid-cavity short axis view, with the segments numbered 7 through 12. The lower apical level short axis view 106 has four segments numbered 13 through 16. Each of these three ultrasound image plane circles is oriented to the anterior side of the heart at the top, to the inferior side of the heart at the bottom, to the septal wall to the left and to the lateral wall of the heart at the right. A final segment 17 may be added for the apex of the heart as shown at 108. These circles are displayed concentrically as an ECG bull's eye graph 110 as shown in FIG. 8b. The concentric bullseye is three dimensional in nature, as it is anatomically oriented around the chart to the four sides of the heart, and from the outer diameter to the center in accordance with different levels of the heart.

In accordance with a further aspect of the present invention, the bullseye chart is annotated with indications of ECG ST elevation values, thus providing an ECG-derived anatomical guide to the location of a possible infarction. The user can consider the bull's eye graph alone, or compare it with a bullet scorecard filled in with ultrasonically-derived values for concurrence as to the location, extent, or severity of a heart abnormality. Preferably an ultrasound bullet scorecard and the ECG bull's eye chart are displayed side-by-side on the same screen so the user can see the correlation of the results of the two different examinations. In the following example, a bull's eye graph is filled in with colors or shades (e.g., FIG. 7) based on both ECG and ultrasound parameters, enabling the clinician to have the benefit of both diagnostic techniques in a single visual display.

Figure 9:
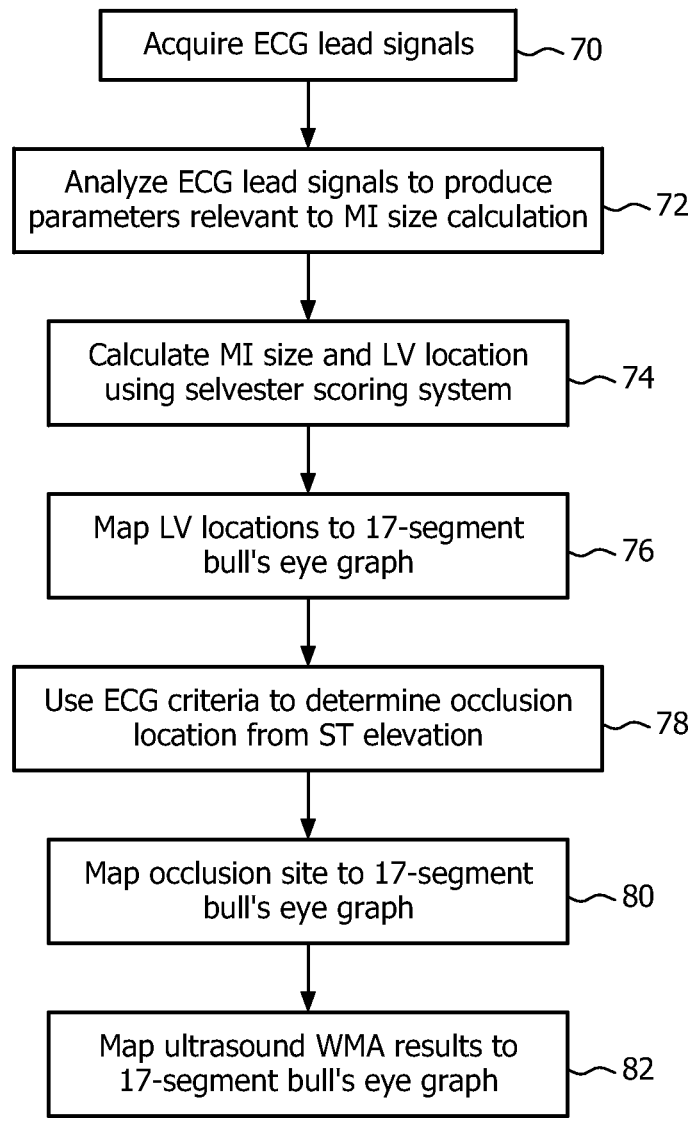
FIG. 9 illustrates a method for producing a bull's eye graph which visualizes MI size in accordance with the principles of the present invention.

FIG. 9 illustrates a method for producing a cardiac imaging style bull's eye graph which utilizes ECG data to visually depict the size of a myocardial infarct that is the area of the heart that has been debilitated by the infarct. The first step 70 is to acquire ECG lead signals of a patient. This may be done with the diagnostic ECG system shown in FIG. 9. In step 72 the ECG lead signals are analyzed to produce parameters relevant to the calculation of the size of a myocardial infarct. This may be done by the ECG analysis module 36 of the diagnostic ECG system described previously. In general, the association of abnormal ECG signals to infarcted locations of the heart as seen in different ultrasound views of the heart is as follows:

TABLE 1

| Ultrasound View: Apical 4-chamber | |
|---|---|
| Location | Leads |
| Septal | V1, V2 |
| Lateral | V5, V6 |

TABLE 2

| Ultrasound View: Apical 2-chamber | |
|---|---|
| Location | Leads |
| Anterior | V3, V4 |
| Inferior | II, III, aVF |

TABLE 3

| Ultrasound View: Short axis mid-cavity | |
|---|---|
| Location | Leads |
| Anteroseptal | aVR, V1, V2 |
| Anterolateral | aVL, I, V5, V6 |
| Inferoseptal | aVF, III, V1, V2 |
| Inferolateral | II, aVF, V5, V6 |

It is understood that the above tables are general in nature and that specific physicians may have differing views on the association of specific ECG leads with specific heart regions. Lead placement on the chest can affect the location assignment. Furthermore, new research may find different associations to be more relevant to specific disease conditions.

ECG interpretation is generated from an expert system with rule based criteria. Automated interpretation provides a comprehensive set of ECG abnormalities that may be relevant to specific disease conditions and can serve as a reference for a clinician to use in diagnosis. For example, when the clinician sees a borderline thickened left ventricular wall in ultrasound imaging, the ECG presentation should exhibit a severely increased R wave amplitude on leads V5 and V6 and an S wave amplitude on leads V1 and V2, leading to an ECG interpretation of "left ventricular hypertrophy". The ECG may add more evidence to confirm left ventricular hypertrophy, which increases the clinician's diagnostic confidence. The same principal applies to right ventricular hypertrophy diagnosis. ECG LVH thresholds are typically related to age-, gender- and race-specific limits. With ultrasound or ECG diagnosis alone, the diagnosis of hypertrophy can be weak and inaccurate. But combined ultrasound and ECG analysis can significantly enhance the diagnostic capability of an exam report. Another example is diagnosing atrial enlargement. An ECG interpretation of left atrial enlargement is based on wide P wave amplitudes in leads V1 and II. Right atrial enlargement is indicated by an inverted P wave in leads aVL and aVR.

Another example of the use of the combined display of ultrasound image analysis and ECG waveform interpretation is in diagnosing conduction abnormalities. For possible cardiac resynchronization therapy, the clinician is looking for indications of left and right bundle branch block. Left bundle blanch block is examined by considering the value of left axis shift of the frontal plane vector of the QRS complex and the QRS duration in excess of 120 msec. For right bundle branch block the clinician is examining the right axis shift of the QRS vector and the QRS duration in excess of 120 msec.

The relevant ECG parameters are used in step 74 to calculate the size of a myocardial infarction and its location in the left ventricle using the Selvester scoring system. The Selvester scoring system uses certain parameters (amplitudes in millivolts, durations in milliseconds) of the QRS complex of the ECG signal. These parameters may be produced by the ECG analysis module 36 as illustrated in FIG. 6 and are then used to estimate the size of a myocardial infarction. See the tables illustrated in "Development of an automated Selvester Scoring System for estimating the size of myocardial infarction from the electrocardiogram" by Horacek et al., J. Electrocardiology 39 (2006) at pp 162-68. First published in 1982 and well validated, the Selvester scoring system identifies the severity of infarction in various locations of the left ventricle. In step 76 the locations of the left ventricle having indications of myocardial infarction are mapped to segments of a 17-segment bull's eye graph 100 as shown in FIG. 8b. Quantified values of ECG parameters or Selvester scores may be annotated on the bull's eye graph, but preferably the affected segments are colored with a first color or shading to indicate segments affected by infarction. In step 78, ECG parameters are used to determine the location of coronary occlusion. Preferably this is done by identifying two or more contiguous leads of a 12-lead ECT which show ST waveform segment elevation. The ECG criteria of A. Bayes de Luna or Wellens are used to determine the location in a coronary artery (proximal or distal) where an occlusion is present. See the texts "The 12 Lead ECG in ST Elevation Myocardial Infarction: A Practical Approach for Clinicians," A. Bayes de Luna et al., Wiley & Sons, New York (2006) and "The ECG in acute myocardial infarction and unstable angina—diagnosis and risk stratification," Hein J J Wellens et al., Kluwer Academic Publishers (2004). In step 80 the identified occlusion sites are mapped to the 17-segment bull's eye graph. Again, the mapped information can be quantified values, but preferably it is done by coloring affected segments with a second color or shading different from the first color or shading. The bull's eye graph thereby provides a visual display to the clinician of the size of a myocardial infarction by the number of bull's eye graph segments which are colored, and in a format which is familiar to echocardiologists. If desired, wall motion abnormalities found by ultrasound imaging can also be annotated on the 17-segment bull's eye graph as indicated by step 82. As above, this is preferably done by annotating segments with a third color or shading to visually identify the ultrasound-derived information to the clinician. The bull's eye graph can be displayed on the cardiograph display 38 when containing only ECG information or on the combined system display 26 when containing ECG information or both ultrasound and ECG information.

Figure 10:
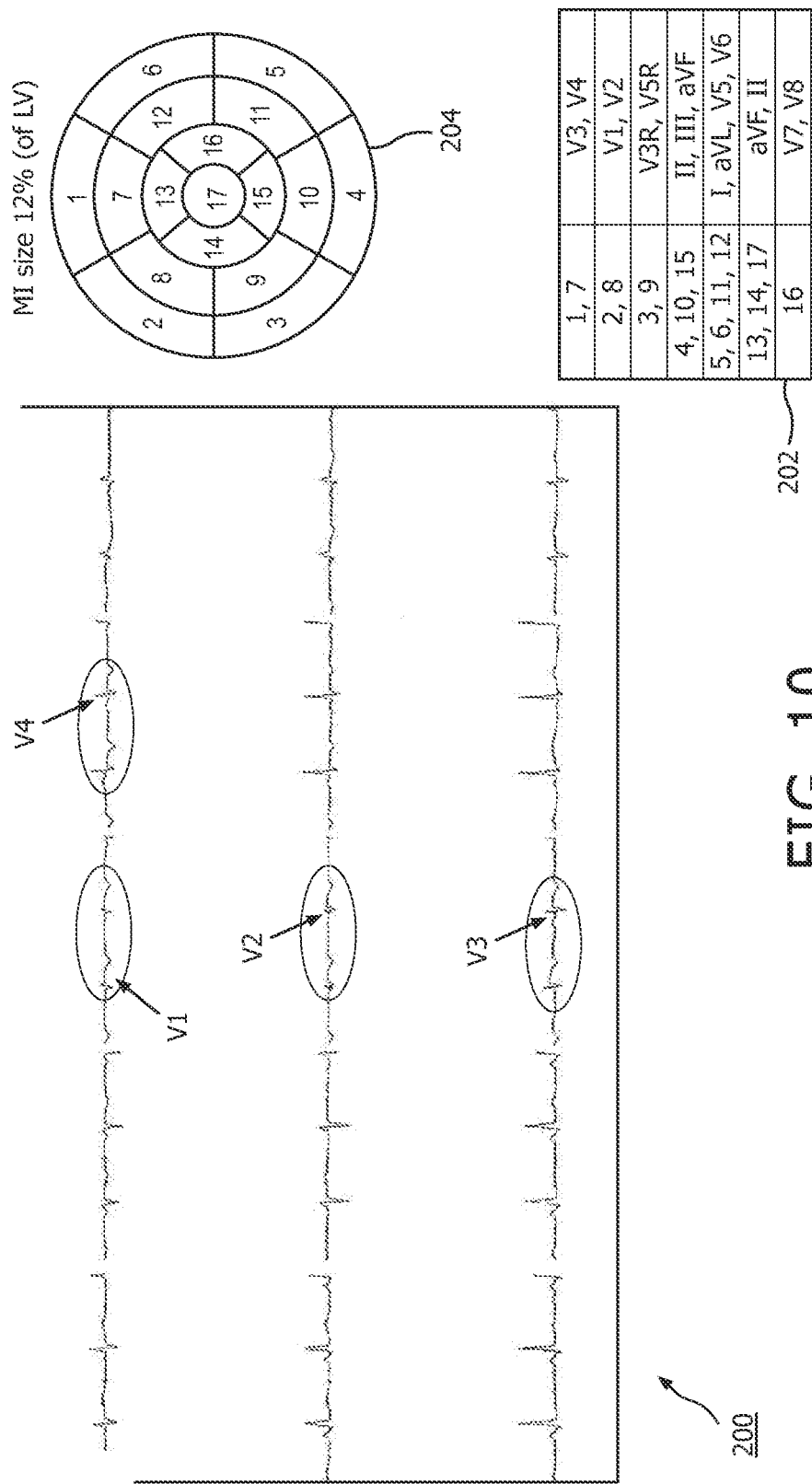
FIGS. 10-12 illustrate displays which visualize the size of a myocardial infarct using a cardiac imaging bull's eye graph filled in with ECG results in accordance with the principles of the present invention.
Figure 11:
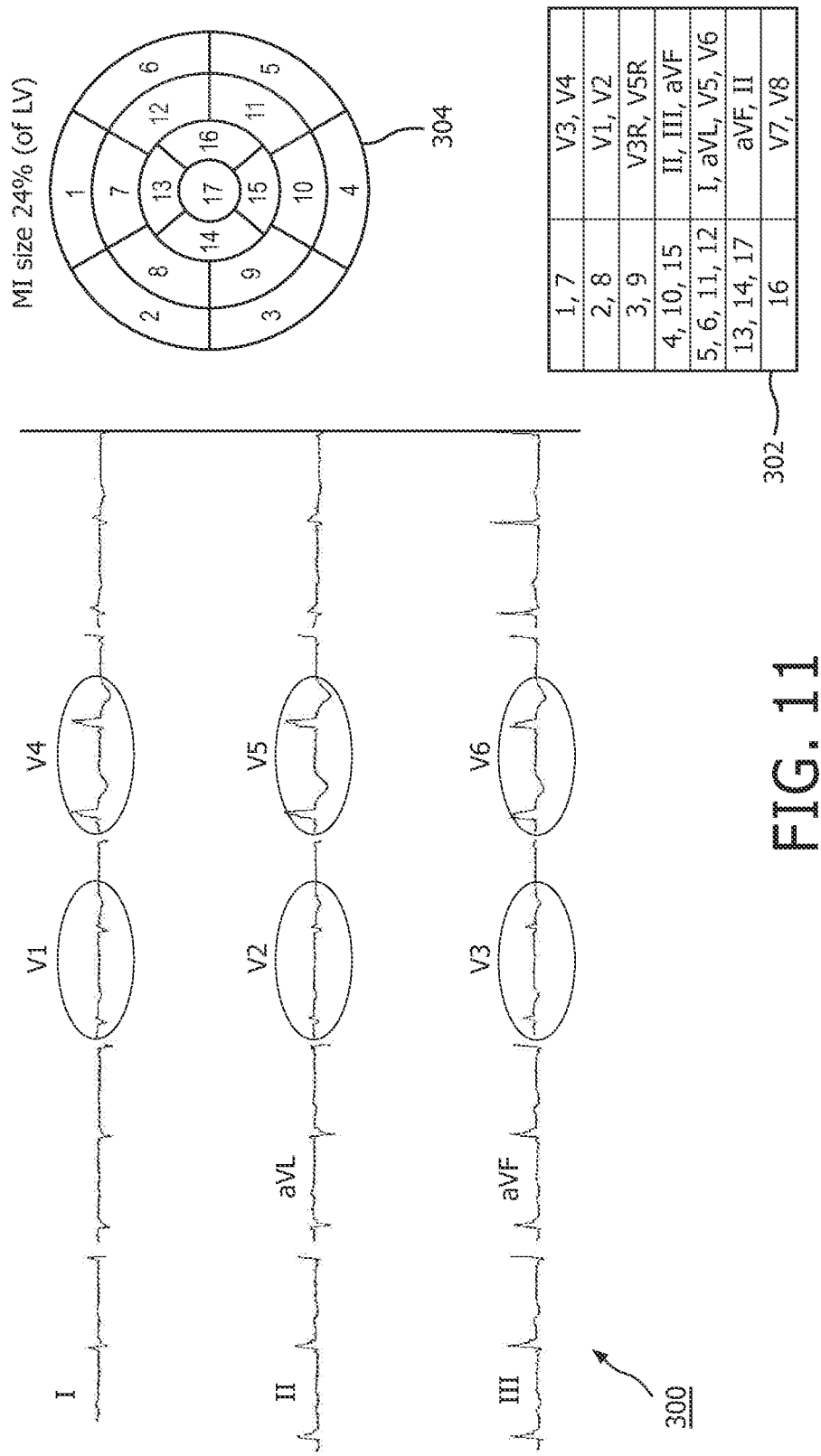
Figure 12:
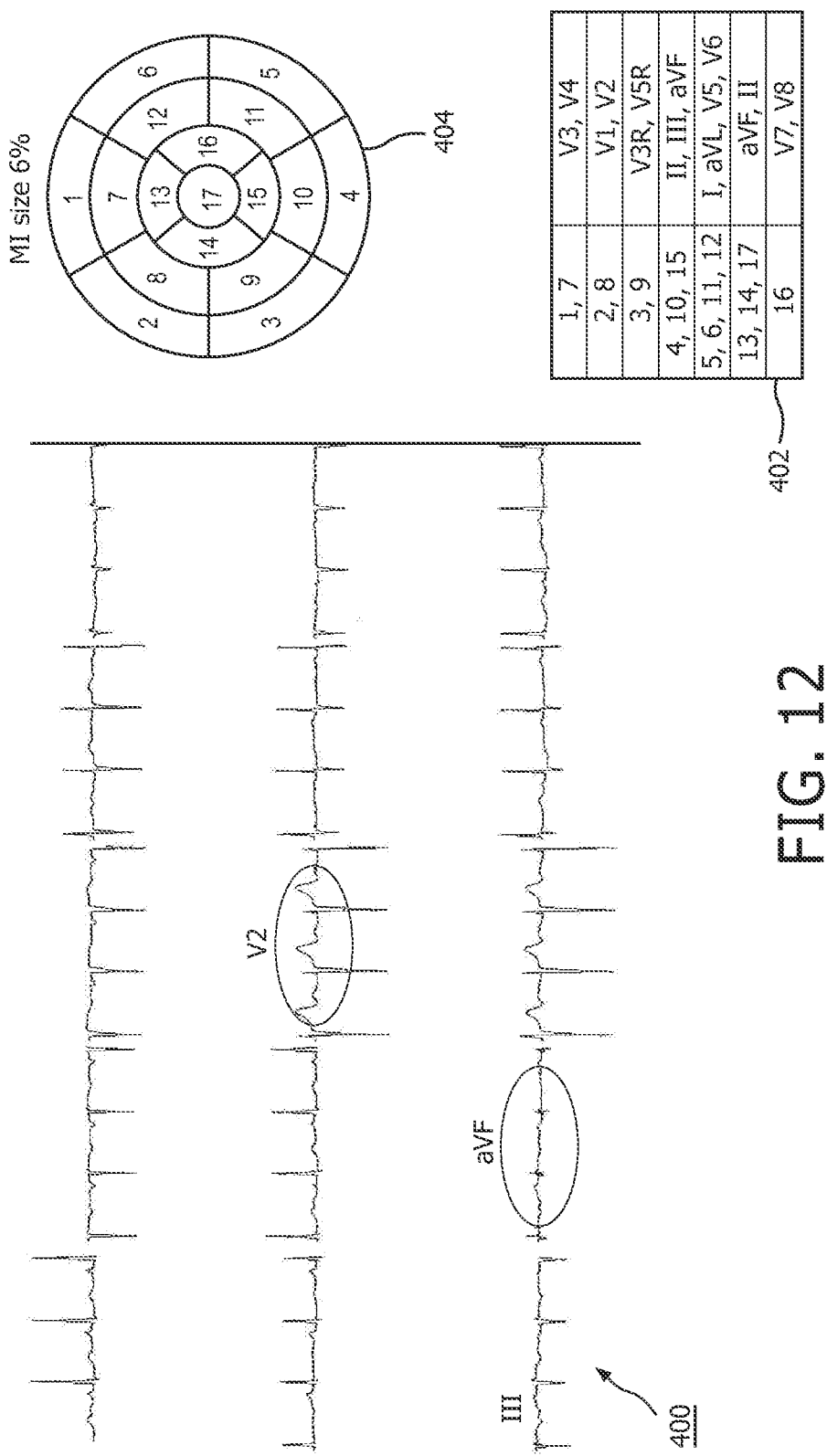

Examples of visual displays of MI size in accordance with the principles of the present invention for actual patient data are shown in FIGS. 10-12. Area 200 of the display contains the lead signals for sixteen leads. The leads of relevance for the MI size display in the bull's eye graph 204 are circled on the ECG area of the display. The anatomical association of the leads to specific segments of the bull's eye graph 204 is shown in the table 202 in the lower right-hand corner of the display. In this example there is the presence of a Q wave in leads V1 and V2, a reduced R wave amplitude in leads V2-V4, and an inverted T wave in leads V1-V5, all indicators of myocardial infarction. Accordingly, using the associations of table 202, segments 1, 2, 7 and 8 are filled with color, providing visual indication of a MI in the septal and anteroseptal regions of the left ventricle. The Selvester size score of 12% is displayed above the bull's eye graph. No ST elevation was exhibited in this ECG.

FIG. 11 shows an ECG of the same patient taken at a later time. The leads of this ECG 300 show the presence of a Q wave V1-V2, reduced R wave amplitude in V2-V3, and an inverted T wave in V1-V5. Also shown is a notch in the R wave in leads V4-V6. The limb leads on the left side of the display (e.g., aVF and III) exhibit a biphasic T wave. Using the relational table 302, these abnormalities are mapped to and color in segments of the bull's eye graph 304. As the visual impression of the bull's eye graph 304 immediately conveys, the size of the patient's MI has increased significantly from that shown in FIG. 10. Again, the Selvester MI size score of 24% is displayed above the bull's eye graph 304. As before, no ST elevation is seen in the interpretation.

FIG. 12 illustrates a display for a patient whose ECG 400 exhibits a giant T wave in lead V2, which is a sign of an evolving posterior MI. The ECG also shows reduced R wave amplitude in leads III and aVF. Again there is no ST elevation nor is a long QT interval present. The table 402 shows that these indications are mapped to segments 4 and 10 of the bull's eye graph 404, which visually indicates a myocardial infarction of the inferior wall of the left ventricle.

What is claimed is:

1. A diagnostic ECG system for visually displaying a size of a myocardial infarction (MI), the system comprising:
    an ECG analysis module responsive to an ECG lead signal and configured to produce parameters corresponding to certain anatomical locations of the heart for which the ECG parameter indicates the MI;
    a bull's eye graph subdivided into a plurality of segments anatomically corresponding to different areas around the left ventricle of the heart and at different levels of the left ventricle in relation to an apex of the heart; and
    an image processor configured to visually distinguish one of the plurality of segments corresponding to anatomical locations of the heart identified by the produced parameters to visually display the size of the MI.

2. The diagnostic ECG system of claim 1, wherein the parameters produced by the ECG analysis module comprise at least one of an R wave amplitude or notch, a P wave amplitude or polarity, a QRS vector axis shift, a Q wave, a T wave, and an ST elevation of an ECG waveform.

3. The diagnostic ECG system of claim 1, wherein the parameters produced by the ECG analysis module further comprise parameters relevant to MI size and left ventricle location using the Selvester scoring system.

4. The diagnostic ECG system of claim 3, wherein the ECG analysis module is further configured to map left ventricle location parameters relevant to MI size to segments of the bull's eye graph.

5. The diagnostic ECG system of claim 4, wherein the ECG analysis module is further configured to mark the segments of the bull's eye graph to which the left ventricle location parameters are mapped with a first distinctive color or shading.

6. The diagnostic ECG system of claim 5, wherein the ECG analysis module is further configured to map a determined location where an occlusion is present to a segment of the bull's eye graph and to mark the segment in a second distinctive color or shading.

7. The diagnostic ECG system of claim 6, further comprising a display device configured to display the size of the MI with the first and second distinctive colors or shadings, and
wherein the display device is further responsive to the ECG analysis module to display the MI size derived from a Selvester scoring system as a percentage value.

8. The diagnostic ECG system of claim 7, wherein the display device is further responsive to the ECG analysis module to simultaneously display a plurality of ECG lead waveforms and the bull's eye graph.

9. The diagnostic ECG system of claim 8, wherein the bull's eye graph further comprises a 17-segment bull's eye graph.

10. The diagnostic ECG system of claim 8, wherein the segments of the bull's eye graph which are visually distinguished by ECG parameter data are visually distinguished by a first color or shading, and a segment which is visually distinguished by WMA data is visually distinguished by a second color or shading.

11. The diagnostic ECG system of claim 1, wherein the ECG analysis module is further configured to determine a location in a coronary artery where an occlusion is present.

12. The diagnostic ECG system of claim 11, wherein the ECG analysis module is further configured to map the determined location where the occlusion is present to a segment of the bull's eye graph.

13. The diagnostic ECG system of claim 1, wherein the ECG analysis module is further configured to determine a location where an occlusion is present using ECG data.

14. The diagnostic ECG system of claim 1, further comprising an ultrasound imaging system configured to analyze heart wall motion abnormalities (WMA) and produce anatomically corresponding WMA data,
wherein an anatomically corresponding segment of the bull's eye graph is further visually distinguished by ultrasonic imaging derived wall motion abnormality data.

\* \* \* \* \*